(12) United States Patent
Rodet et al.

(10) Patent No.: US 11,565,038 B2
(45) Date of Patent: Jan. 31, 2023

(54) PUMP DEVICE COMPRISING A STORAGE DEVICE FOR RECEIVING A HANDSET

(71) Applicant: Fresenius Vial SAS, Brézins (FR)

(72) Inventors: Jean Rodet, Nantoin (FR); Thibault Cretinon, Tassin la Demi Lune (FR); Florie Perrigouard, St. Etienne de St. Geoirs (FR); Yann Mirek, Bourgoin Jallieu (FR); Remi Duprez, Coublevie (FR)

(73) Assignee: Fresenius Vial SAS, Brézins (FR)

( * ) Notice: Subject to any disclaimer, the term of this patent is extended or adjusted under 35 U.S.C. 154(b) by 143 days.

(21) Appl. No.: 16/615,020

(22) PCT Filed: Mar. 22, 2018

(86) PCT No.: PCT/EP2018/057224
§ 371 (c)(1),
(2) Date: Nov. 19, 2019

(87) PCT Pub. No.: WO2018/215116
PCT Pub. Date: Nov. 29, 2018

(65) Prior Publication Data
US 2020/0078512 A1 Mar. 12, 2020

(30) Foreign Application Priority Data
May 24, 2017 (EP) .................................. 17305613

(51) Int. Cl.
*A61M 5/145* (2006.01)
*A61M 5/14* (2006.01)
(52) U.S. Cl.
CPC ........ *A61M 5/1452* (2013.01); *A61M 5/1413* (2013.01)

(58) Field of Classification Search
CPC ......... A61B 50/20; A61B 50/24; A61B 50/26; H02G 11/00; H02G 11/02
See application file for complete search history.

(56) References Cited

U.S. PATENT DOCUMENTS 5,069,668 A * 12/1991 Boydman ............. A61M 5/172
604/121
5,415,287 A * 5/1995 Hamano ................ A61B 1/121
128/DIG. 26

(Continued)

FOREIGN PATENT DOCUMENTS

| CN | 1174514 | 2/1998 |
|----|---------|--------|
| CN | 204766828 | 11/2015 |

(Continued)

OTHER PUBLICATIONS

International Search Report and Written Opinion, counterpart International Appl. No. PCT/EP2018/057224 (dated Jun. 20, 2018) (13 pages).

(Continued)

*Primary Examiner* — Laura A Bouchelle
(74) *Attorney, Agent, or Firm* — Cook Alex Ltd.

(57) ABSTRACT

A pump device (1) for administering a medical fluid to a patient (4), comprises a housing 5 (10), a pumping mechanism (12) for pumping a medical fluid through an infusion line (3) toward a patient (4), and a handset (16) for entering a control command for controlling an operation of the pumping mechanism (12). Herein, a storage device (15) is arranged on the housing (10) and comprises a receptacle (150) defining a cavity (151) therein for receiving the handset (16). In this way a pump device is provided which allows for improved comfort in particular when using the pump device in a healthcare environment, for example at the bedside of a patient.

6 Claims, 4 Drawing Sheets

(56) References Cited

U.S. PATENT DOCUMENTS

| | | | |
|---|---|---|---|
| 5,573,506 A | 11/1996 | Vasko | |
| 6,355,018 B1 | 3/2002 | Vasko | |
| D529,489 S * | 10/2006 | Sbordon, Jr. | ................ D14/253 |
| 7,879,008 B2 * | 2/2011 | Haury | ............... A61M 5/16804 |
| | | | 604/151 |
| 7,935,077 B2 * | 5/2011 | Thor | ...................... A61B 50/10 |
| | | | 604/67 |
| 2005/0177111 A1 | 8/2005 | Ozeri et al. | |
| 2007/0255116 A1 | 11/2007 | Mehta et al. | |
| 2010/0030132 A1 * | 2/2010 | Niezgoda | .............. A61L 2/0088 |
| | | | 604/22 |
| 2014/0121845 A1 | 5/2014 | Mueller | |
| 2014/0194817 A1 | 7/2014 | Lee et al. | |
| 2015/0352284 A1 * | 12/2015 | Simmons | ............... G16H 20/17 |
| | | | 604/67 |

FOREIGN PATENT DOCUMENTS

| | | |
|---|---|---|
| WO | WO03/068295 | 8/2003 |
| WO | WO2012/049263 A1 | 4/2012 |
| WO | WO2013/126318 A1 | 8/2013 |
| WO | WO2015/062926 A1 | 5/2015 |

OTHER PUBLICATIONS

Office Action with English translation, counterpart Chinese App. No. 201880034085.1 (dated Jun. 1, 2021) (12 pages).

Search Report, counterpart Chinese App. No. 201880034085.1 (dated May 24, 2021) (2 pages).

* cited by examiner

PUMP DEVICE COMPRISING A STORAGE DEVICE FOR RECEIVING A HANDSET

The present application is a U.S. National Stage of PCT International Patent Application No. PCT/EP2018/057224, filed Mar. 22, 2018, which claims priority to EP Application No. 17305613, filed May 24, 2017, both of which are hereby incorporated herein by reference.

The invention relates to a pump device for administering a medical fluid to a patient according to the preamble of claim 1.

A pump device of this kind comprises a housing, a pumping mechanism for pumping a medical fluid through an infusion line towards a patient, and a handset for entering a control command for controlling an operation of the pumping mechanism, the handset being connected to the housing for example via a connection cable.

A pump device of this kind may for example be constituted as a volumetric (peristaltic) infusion pump or as a syringe infusion pump. Within a volumetric infusion pump, the pump mechanism, for example comprising a wobbling device as described for example in W0 2012/049263 A1, acts onto a pumping module of an infusion line for peristaltically pumping fluid through the infusion line towards a patient. Within a syringe infusion pump, a pumping mechanism, for example comprising a pusher device as for example disclosed in WO2015/062926 A1, acts onto a piston of a syringe for pushing the piston into a cylindrical barrel of the syringe in order to deliver a fluid from the cylindrical barrel towards a patient.

A pump device of this kind typically is controlled by an electronic control device which controls the pumping mechanism in order to deliver a defined dosage of a medical fluid at a set dose rate. Via the handset, herein, additional control commands may be entered by a user, for example to effect the administration of a bolus. For this, the handset for example may comprise a pushbutton which the user may press in order to enter a control command.

The handset generally is a piece of equipment which can manually be handled by a user by grabbing it and by actuating an actuation element of the handset such as a pushbutton. The handset is operatively connected to the housing of the pump device and to the control device enclosed in the housing for example via a connection line, the connection line being constituted to electrically transmit signals in between the handset and the control device. Alternatively, it also is conceivable that the handset is connected to the control device wirelessly by a suitable wireless data communication connection.

It is an object of the instant invention to provide a pump device which allows for an improved comfort in particular when using the pump device in a healthcare environment, for example at the bedside of a patient.

This object is achieved by means of a pump device comprising the features of claim 1.

Accordingly, the pump device comprises a storage device arranged on the housing and comprising a receptacle defining a cavity therein for receiving the handset.

By means of the storage device the handset may be placed on the housing of the pump device in an organized fashion. The storage device comprises a receptacle defining a cavity therein, the cavity being formed and shaped such that the handset may be placed within the cavity and, when placed in the cavity, is held on the housing of the pump device in a secure and organized manner.

By means of the storage device the handset, when not in use, hence may be fixedly held on the housing of the pump device. This increases the comfort for use because the handset is received in a defined place on the housing of the pump device and hence does not disturb normal operation and use of the pump device.

The receptacle may, in one embodiment, comprise an exit opening for guiding a connection cable out of the receptacle, the connection cable providing for an (electrical) connection of the handset to a control device enclosed in the housing. Via the exit opening the connection cable hence may be guided out of the receptacle towards the housing for connection to the housing.

The exit opening, in one embodiment, may be arranged on a bottom end of the receptacle, wherein the receptacle is open towards a top end opposite the bottom end such that the handset may be inserted into the cavity defined by the receptacle through the top end. In this case for example an opening in the shape of a slit is arranged on the receptacle through which the connection cable may be inserted into the receptacle when placing the handset in the receptacle.

In another embodiment, the storage device may comprise a cable storage around which the connection cable can be wound. The cable storage serves to receive the connection cable such that the connection cable may be arranged and maintained on the housing of the pump device in an organized fashion.

The cable storage, in one embodiment, may be integrally formed with the receptacle. For example, the connection cable may be wound around the receptacle such that the connection cable can be stored on the receptacle.

In one embodiment, the cable storage comprises a body around which the connection cable can be wound, the body being attached to the housing and extending from the housing such that the connection cable may be placed around the body. In order to store the connection cable in a defined manner on the body, an outer rim may radially protrude from the body such that the body, at a far end pointing away from the housing, is confined by the outer rim. The cable storage hence provides for a confined space in which the connection cable may be stored in an organized fashion.

In one embodiment, the pumping mechanism is arranged on a front side of the housing. For example, in case of a volumetric (peristaltic) infusion pump a pumping mechanism comprising a wobbling device or the like may be placed on the front side of the housing for acting onto an infusion line placed and received on the front side of the housing. In case of a syringe infusion pump a syringe may be received on the front side of the housing, a pusher device being guided along the front side for acting onto the syringe. Herein, in one embodiment, the storage device is arranged on a back side of the housing opposite the front side such that, when received in the receptacle, the handset is stored and maintained on the housing in a location removed from the pumping mechanism such that the handset and a connection cable extending from the handset may not interfere with a pumping operation.

In another embodiment, the connection cable comprises a connector by which the connection cable is attached to the housing at a bottom side of the housing. The connector may for example provide for a releasable connection to the housing, the connector being formed for example by a plug connector which can be arranged in a suitable socket arranged on the housing. By connecting the connector to the housing in the region of a bottom side of the housing it can be ensured that the connection cable, at its connection location, is not in the way when conventionally operating the pump device.

In a specific embodiment the pump device is constituted as a syringe infusion pump comprising a pumping mechanism including a pusher device for acting onto a syringe placed on the pump device. By moving a piston of the syringe a medical fluid may be delivered from the syringe towards a patient. The pusher device herein is guided along a guide device arranged on a housing section of the housing such that the pusher device is translationally movable along the housing for pushing the piston into a cylindrical barrel of the syringe.

In one embodiment, the storage device for receiving the handset herein may be arranged on said housing section, for example on a back side of said housing section opposite the guide device guiding the pusher device.

The idea underlying the invention shall subsequently be described in more detail with respect to the embodiments shown in the figures. Herein:

Figure 1:
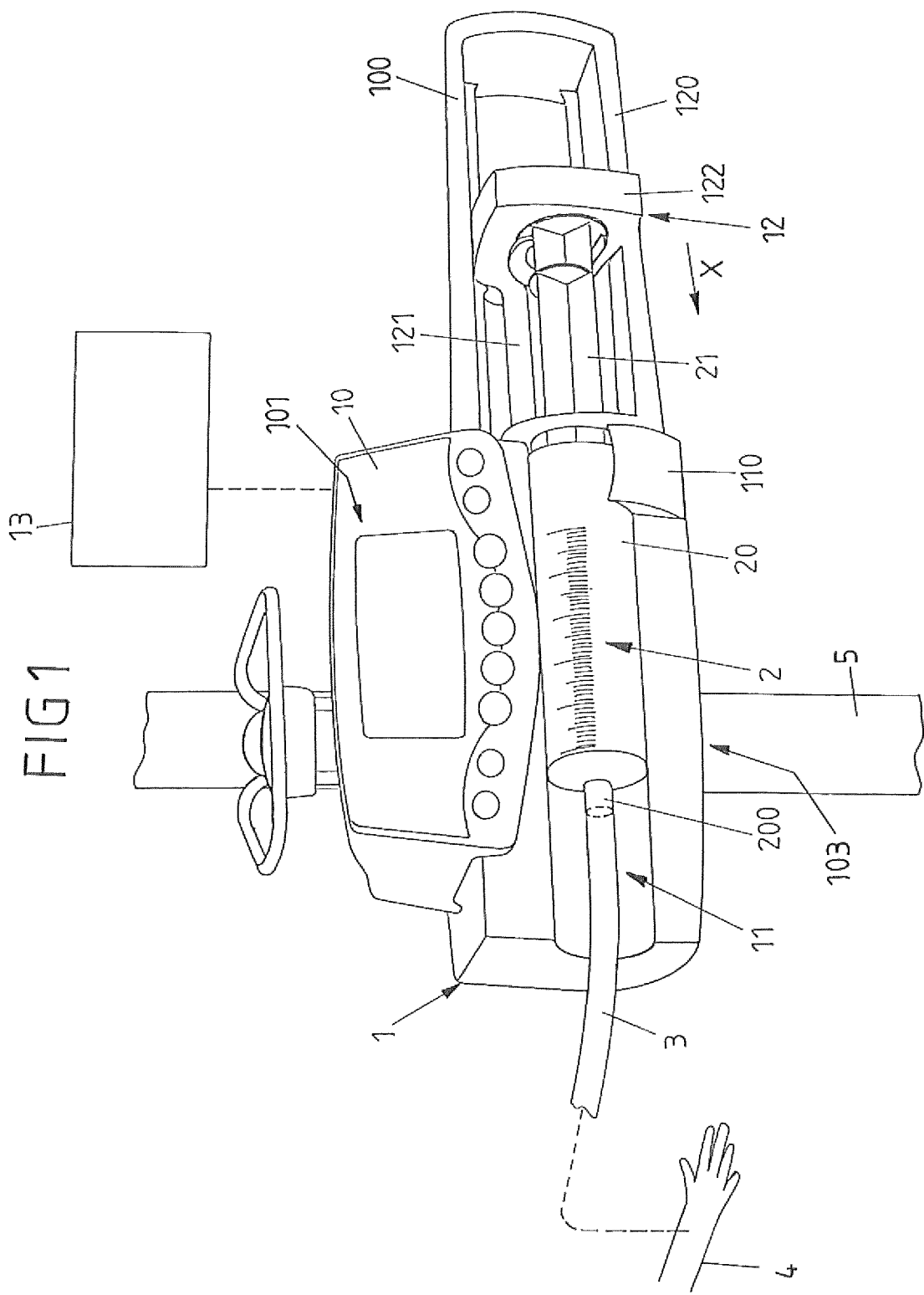
FIG. 1 shows a view of an embodiment of an infusion device in the shape of a syringe pump.

FIG. 1 shows an embodiment of an infusion device 1 in the shape of a syringe pump having a housing 10 and a receptacle 11 arranged on the housing 10 to receive a syringe 2 therein.

The syringe 2 comprises a cylindrical tube 20 which, when installing the syringe 2 on the infusion device 1, contains a medical liquid, for example a medication, to be infused to a patient 4. The cylindrical tube 20 is connected, via a connector 200, to an infusion line 3 which may extend from the syringe 2 towards a patient 4 for infusing the medical liquid to the patient 4.

For installing the syringe 2 on the receptacle 11 of the infusion device 1, the cylindrical tube 20 of the syringe 2 is placed in the receptacle 11 and is mechanically connected to the housing 10 by means of a fixation device 110. By means of the fixation device 110, for example constituted by a releasable clamp element, the cylindrical tube 20 is secured within the receptacle 11 such that the cylindrical tube 20 is held in position on the receptacle 11.

The syringe 2 comprises a piston 21 which, for delivering medical fluid contained in the cylindrical tube 20, can be pushed into the cylindrical tube 20 in a pushing direction X. For this, the infusion device 1 comprises a pumping mechanism 12 having a pusher device 122 movably arranged within a guide device 120 and connected to a suitable drive mechanism via a connecting rod 121.

For operating the infusion device 1, the syringe 2 is installed on the infusion device 1 and, for performing an infusion process, the pusher device 122 is electrically moved, controlled by a control device 13 of the infusion device 1, in the pushing direction X to move the piston 21 into the cylindrical tube 20 for delivering the medical fluid contained in the cylindrical tube 20 via the infusion line 3 towards the patient 4.

Figure 2:
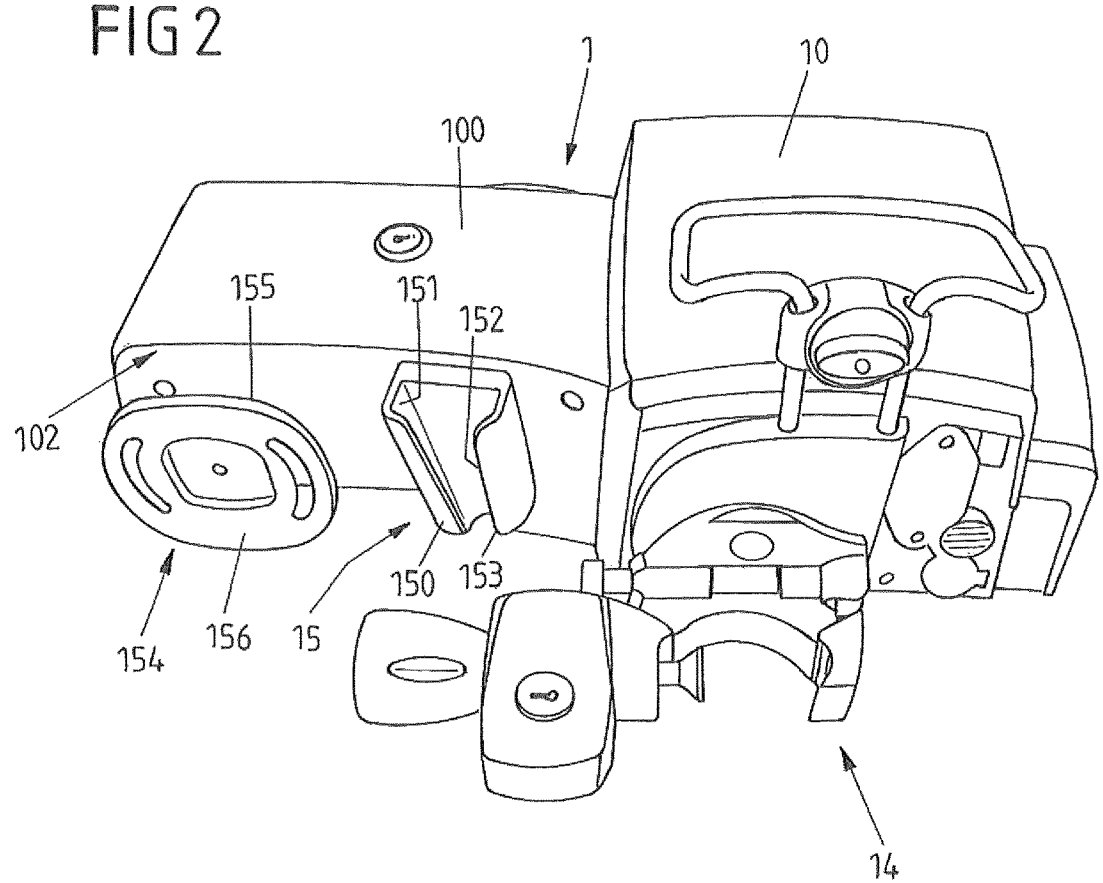
FIG. 2 shows a back-side view of a pump device according to a first embodiment.
Figure 3:
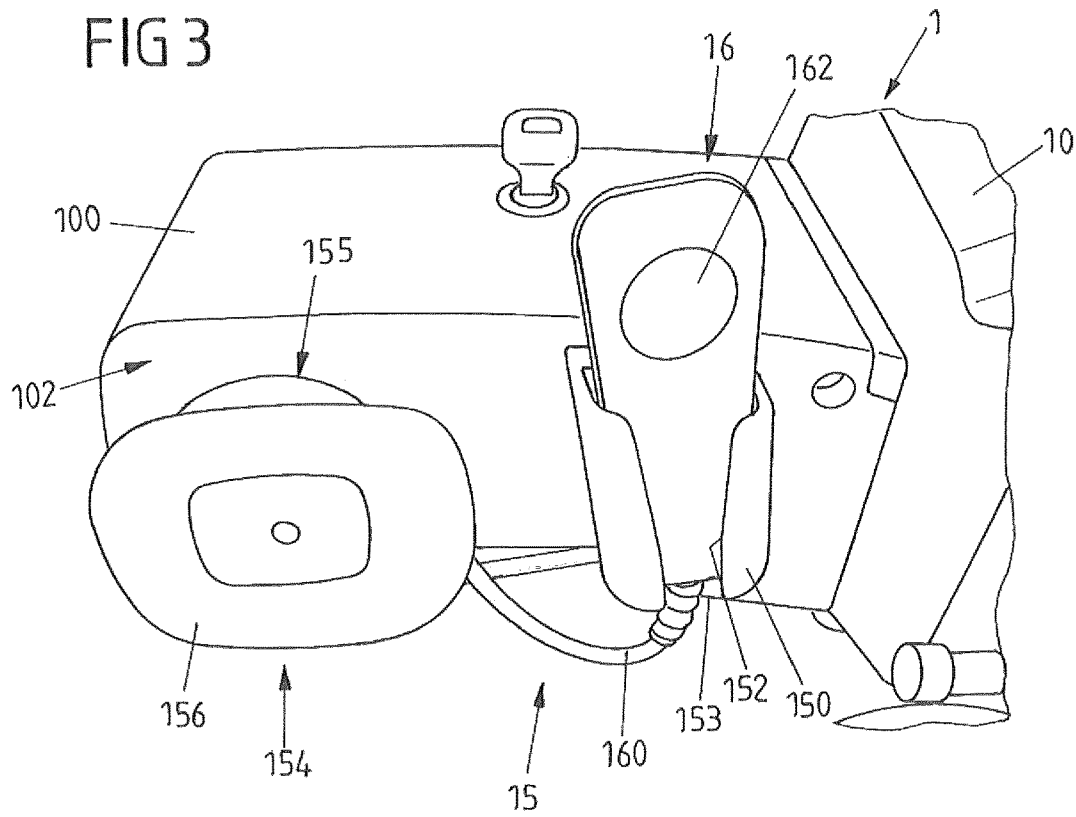
FIG. 3 shows another view of the pump device, showing in particular a storage device for receiving a handset of the pump device and a connection cable connected to the handset.
Figure 4:
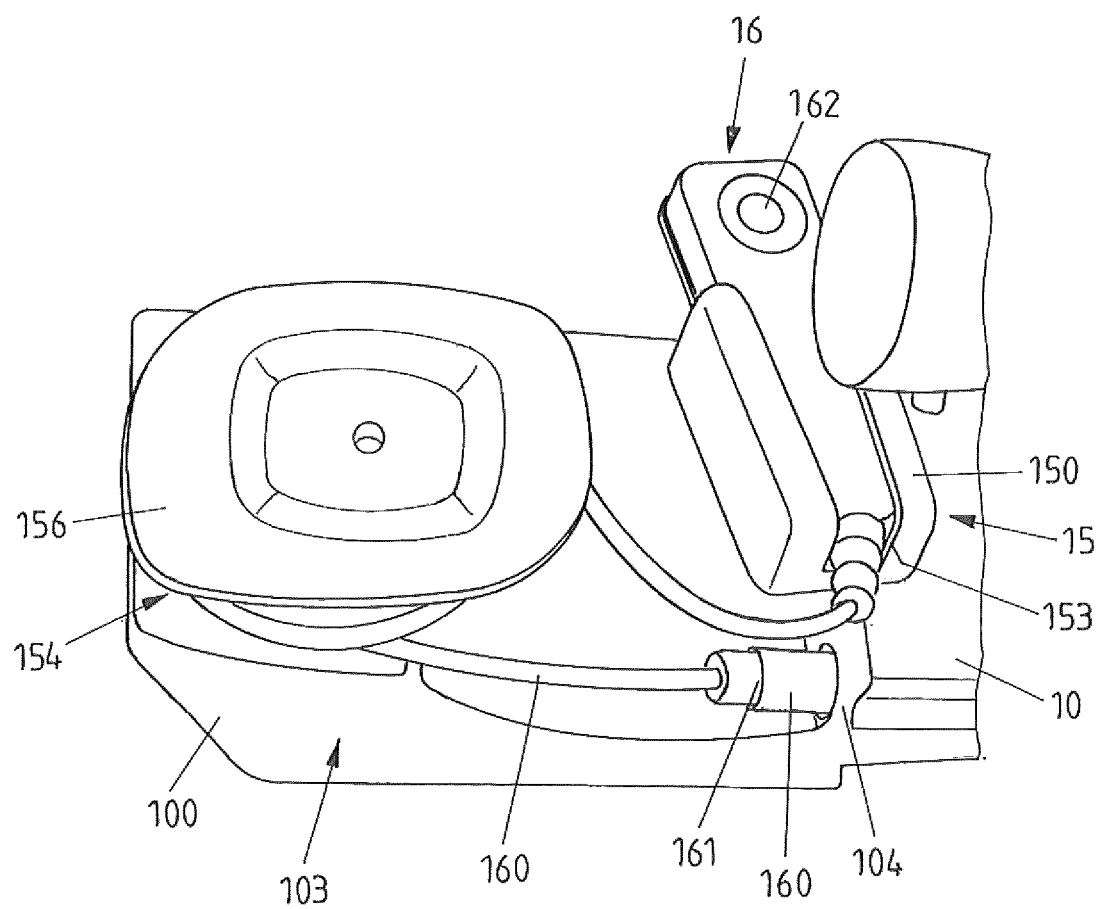
FIG. 4 shows another view of the storage device of the pump device.

FIGS. 2 to 4 show views of an embodiment of a pump device 1 for example constituted as a syringe pump of the type shown in FIG. 1. The pump device 1, via a fixation device 14, may be arranged on a stand 5 (see FIG. 1) such that the pump device 1, in combination for example with other pump devices 1, may be arranged and held at the bedside of a patient.

The pump device 1 comprises a handset 16 which is connected to the housing 10 of the pump device 1 via a connection cable 160 and comprises a pushbutton 162 which a user may push in order to issue a control command such as for example a command to administer a bolus to a patient.

The handset 16 may be manually grabbed by a user and serves to input control commands into the pump device 1. The handset 16 generally may have one or multiple actuation elements such as pushbuttons 162 and can be removed from the housing 10 in order to allow a user, for example a patient, to enter input commands into the pump device 1.

Via the connection cable 160 the handset 16 is connected to the control device 13 of the pump device 1 such that signals may be transmitted in between the handset 16 and the control device 13, in particular data signals affecting the operation of the pump device 1.

As visible for example from FIG. 4, the connection cable 160, via a connector 161, is connected to a suitable connector 104 of the housing 10 at a bottom side 103 of the housing 10, the bottom side 103 facing downwards in a normal, intended state of operation of the pump device 1.

The guide device 120 for guiding the pusher device 122 along the movement direction X is formed on a housing section 100 of the housing 10. At a back side 102 of the housing section 100 a storage device 15 is arranged and integrally formed with the housing section 100, the storage device 15 serving to store the handset 16 and to receive the connection cable 160.

The storage device 15 comprises a receptacle 150 defining a cavity 151 therein into which the handset 16 may be inserted. The receptacle 150 at its outer circumference comprises an opening 152 in the shape of a slit which extends generally vertical along the receptacle and at a bottom end facing the bottom side 103 of the housing section 100 terminates in an exit opening 153 through which the connection cable 160 may exit from the cavity 151 formed in the receptacle 150. The handset 16 may be placed in the cavity 151 of the receptacle 115 in a generally upright position and for this may be inserted into the receptacle 150 through a top end opposite the bottom end of the receptacle 150.

The receptacle 150 serves to hold and maintain the handset 16 when not in use. By means of the receptacle 150 the handset 16 hence may be placed in a defined location and position on the housing 10 of the pump device 1 such that it is maintained in an organized fashion on the pump device 1.

Whereas the pumping mechanism 12 is arranged on a front side 101 of the housing 10, the storage device 15 is formed on the back side 102 of the housing section 100. Because the handset 16 is stored in the receptacle 150 of the storage device 15 on the back side 102 of the housing section 100, the handset 16, when stored in the receptacle 150, does not interfere with the regular pumping operation of the pump device 1, in particular the pumping mechanism 12.

The storage device 15 furthermore comprises a cable storage 154 formed by a body 155 around which the connection cable 160 may be wound, as shown in FIGS. 3 and 4.

The body 155, which may have a generally cylindrical shape, is confined at a far end facing away from the housing section 100 by an outer rim 156 radially protruding from the body 155 such that the connection cable 160 wound around the body 155 may not easily slip from the body 155.

By means of the storage device 15, hence, also the connection cable 160 may be arranged and maintained on the pump device 1 in an organized fashion.

For using the handset 16, the handset 16 may be removed from the receptacle 150, and the connection cable 160 may be unwound from the cable storage 154.

Figure 5:
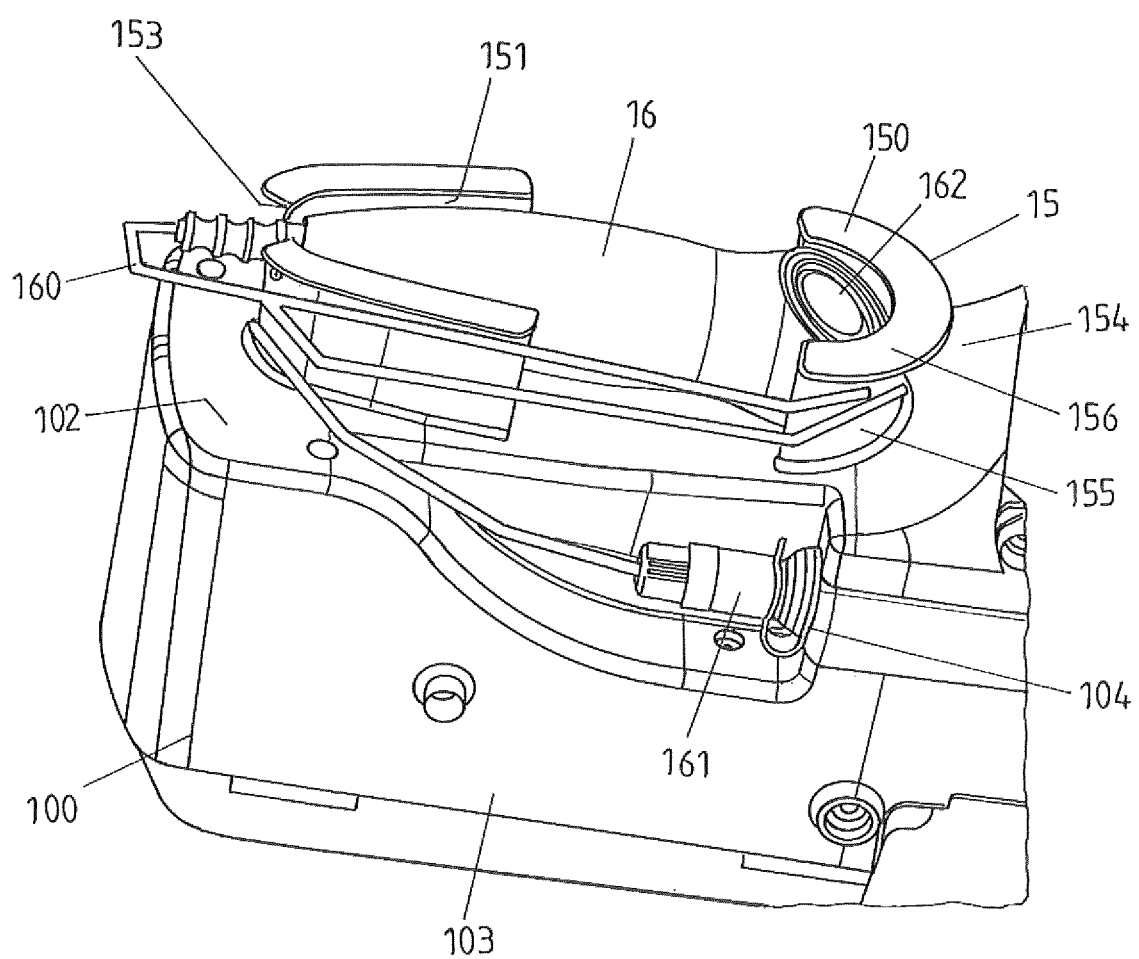
FIG. 5 shows a storage device of a pump device according to a different embodiment.

Whereas in the embodiment of FIGS. 2 to 4 the cable storage 154 and the receptacle 150 are formed as separate units on the housing 10, in the embodiment of FIG. 5 a cable storage 154 and a receptacle 150 are integrally formed by a single functional unit.

In particular, in the embodiment of FIG. 5 a receptacle 150 defines a cavity 151 in which a handset 16 may be placed and may be held by for example providing for a suitable clips connection within the cavity 151. The receptacle 150 is arranged at the back side 102 of the housing section 100 and defines an exit opening 153 through which a connection cable 160 connecting the handset 16 to the housing 10 may exit from the receptacle 150. The cavity 151 is open towards the back such that the handset 16 may be placed in the receptacle 150 in an insertion direction substantially perpendicular to a back face of the housing section 100 forming the back side 102.

The receptacle 150 forms a body 155 for the cable storage 154 around which the connection came 160 may be wound, as it is shown in FIG. 5. The body 155 is confined towards the outside by an outer rim 156 transversely protruding from the body 155 such that the connection cable 160 is held and maintained on the body 155 when wound around the body 155.

The idea underlying the invention is not limited to the embodiments described above, but may be implemented in an entirely different fashion.

It is conceivable to connect a handset by means of a wireless data connection to a pump device. In that case, a cable storage may be dispensable, the handset however being received in a receptacle of a suitable storage device.

The handset may serve to enter control commands of a single or multiple different types. Via the handset for example a command for issuing a bolus may be entered.

A storage device of the kind described above may be used on pump devices of different types for administering medical fluids to patients, for example constituted as volumetric infusion pumps or syringe infusion pumps.

LIST OF REFERENCE NUMERALS

1 Infusion device
10 Housing
100 Housing section
101 Front side
102 Back side
103 Bottom side
104 Connector
11 Receptacle
110 Fixation device
12 Pumping mechanism
120 Guide device
121 Connecting rod
122 Pusher device
13 Control device
14 Fixation device
15 Storage device
150 Receptacle
151 Cavity
152 Opening
153 Exit opening
154 Cable storage
155 Body
156 Outer rim
16 Handset
160 Connection cable
161 Connector
162 Push button
2 syringe
20 Cylinder tube
200 Connector
21 Piston
3 Infusion line
4 Patient
5 Stand
X Movement direction

The invention claimed is:

1. A pump device for administering a medical fluid to a patient, comprising:
   a housing having a front side and a back side opposite the front side,
   a pumping mechanism for pumping a medical fluid through an infusion line toward a patient, the pumping mechanism disposed on the front side of the housing and comprising an exposed pusher device for acting onto a syringe for administering a medical fluid from the syringe towards a patient,
   a handset for entering a control command for controlling an operation of the pumping mechanism, the handset having a proximal end and a distal end,
   a storage device arranged on the back side of the housing and comprising a receptacle defining a cavity configured to receive the distal end of the handset therein, the distal end of the handset disposed therein, and
   a fixation device arranged on the back side of the housing and comprising a clamp with a handle attached to a moveable jaw cooperable with a stand, the clamp used to fix the pump device to the stand,
   wherein the distal end of the handset is connected to the housing via a connection cable, and the receptacle comprises an exit opening configured to guide the connection cable out of the cavity, the connection cable being received therethrough with the distal end of the handset disposed in the cavity, and
   wherein the storage device comprises a cable storage around which the connection cable can be wound with the connection cable attached to the housing, the cable storage comprising a body around which the connection cable can be wound, and the body extends from the housing and is confined, at a far end pointing away from the housing, by an outer rim protruding from the body,
   wherein the receptacle also is confined, at a far end pointing away from the housing, by an outer wall in which the exit opening is formed, neither the outer rim of the cable storage nor the outer wall of the receptacle in interference with the handle of the clamp.

2. The pump device according to claim 1, wherein the exit opening is arranged on a bottom end of the receptacle, and the receptacle is open towards a top end opposite the bottom end such that the distal end of the handset is insertable into the cavity defined by the receptacle through the top end.

3. The pump device according to claim 1, wherein the cable storage is integrally formed with the receptacle.

4. The pump device according to claim 1, wherein the connection cable comprises a connector by which the connection cable is attached to the housing at a bottom side of the housing.

5. The pump device according to claim 1, wherein the handle is disposed a first distance pointing away from the housing, the outer rim protrudes a second distance point pointing away from the housing, and the outer wall protrudes a third distance point away from the housing, wherein the second and third distances are smaller than the first distance.

6. The pump device according to claim 1, wherein the handle is disposed a first distance pointing away from the housing, the outer rim comprises the outer wall, and the outer rim and outer wall protrude a second distance point pointing away from the housing, wherein the second distance is smaller than the first distance.

\* \* \* \* \*